US006482798B2

(12) United States Patent
Schröder et al.

(10) Patent No.: US 6,482,798 B2
(45) Date of Patent: *Nov. 19, 2002

(54) APROTININ VARIANTS HAVING IMPROVED PROPERTIES

(75) Inventors: Werner Schröder, Wuppertal (DE); Søren Bjørn, Lyngby (DK); Kjeld Norris, Hellerup (DK); Viggo Diness, Charlottenlund (DK); Leif Nørksov-Lauritsen, Tappernøje (DK); Niels Dyhr Christensen, Kopenhagen (DK)

(73) Assignee: Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 141 days.

(21) Appl. No.: 08/896,322

(22) Filed: Jul. 17, 1997

(65) Prior Publication Data

US 2002/0103334 A1 Aug. 1, 2002

(30) Foreign Application Priority Data

Jul. 25, 1996 (DE) .......................... 196 29 982

(51) Int. Cl.$^7$ .................. C07K 14/81; A61K 38/55; A61K 38/57
(52) U.S. Cl. .................. 514/12; 530/300; 530/324; 536/23.1; 536/23.5; 435/69.2; 435/255.2; 435/320.1
(58) Field of Search .................. 435/69.2, 255.2, 435/320.1; 530/300, 324; 536/23.1, 23.5; 514/12

(56) References Cited

U.S. PATENT DOCUMENTS

| 4,595,674 A | 6/1986 | Tschesche et al. ............. 514/9 |
| 5,118,668 A | 1/1992 | Auerswald et al. ............ 514/12 |
| 5,164,482 A | 11/1992 | Ebbers et al. ................ 530/324 |
| 5,231,010 A | 7/1993 | Ebbers et al. ............... 435/69.2 |
| 5,591,603 A | 1/1997 | Bjørn et al. ................. 435/69.2 |
| 5,621,074 A | 4/1997 | Bjørn et al. ................. 530/324 |

FOREIGN PATENT DOCUMENTS

| EP | 132732 | 2/1985 |
| EP | 339942 | 11/1989 |
| EP | 419878 | 4/1991 |
| WO | 89/02463 | 3/1989 |
| WO | 90/10075 | 9/1990 |
| WO | 92/0611 | 4/1992 |
| WO | 92/06111 | 4/1992 |

OTHER PUBLICATIONS

Deng, et al., Anal. Biochem., 200, pp. 81–88, "Site–Directed Mutagenesis of Virtually Any Plasmid by Eliminating a Unique Site",(1992).
J.G. Bieth, Biochemical Medicine, 32, pp. 387–397, "In Vivo Significance of Kinetic Constants of Protein Proteinase Inhibitors", (1984).
U.K. Laemmli, Nature 227, pp. 680–685, "Cleavage of Structural Proteins during the Assembly of the Head of Bacteriophage T4", (1970).
C.R. Merril, M.L. Dunau, D. Goldmann, Anal. Biochem. 110, pp. 201–207," A Rapid Sensitive Silver Stain for polypeptides in Polyacrylamide Gels", (1981).
J. Kurjan and Herskowitz, Cell, 30, pp. 933–943, "Structure of a Yeast Pheromone Gene (Mfα)–Factor Precursor Contains Four Tandem Copies of Mature α–Factor", (1982).
Yarger, et al., Mol. Cell. Biol., 6, pp. 1095–1101, "Transcription Terminator–Like Element within a *Saccharomyces cerevisiae* Promotor Region", (1986).
W. Gebbhard, H. Tschesche and H. Fritz, Proteinase Imhibitors, Barrett and Salvesen (eds.), Elsevier Science Publ. BV 375–387, "Biochemistry of aprotinin and aprotinin–like inhibitors", (1986).
Wlodawer, et al., J. Mol. Biol. 198, (1), pp. 227–231, "Structure of Form III Crystals of Bovine Pancreatic Trypsin Inhibitor", (1987).
Berndt, et al., Biochemistry 32 (17), pp. 4564–4570, "Designed Replacement of an Internal Hydration Water Molecule in BPTI: Structural and Functional Implications of a Glycine–to–Serine Mutation", (1993).
Wagner, et al., J. Mol. Biol. 196, (1), pp. 227–231, "Reinvestigation of the Aromatic Side–chains in the Basic Pancreatic Trypsin Inhibitor by Heteronuclear Two–dimensional Nuclear Magnetic Resonance", (1987).
D. Royston, J. Cardithorac, Vasc. Anesth. 6; pp. 76–100, "High–Dose Aprotinin Therapy: A Review o the First Five Years' Experience", (1992).

*Primary Examiner*—Rebecca E. Prouty
(74) *Attorney, Agent, or Firm*—Kurt G. Briscoe; Norris McLaughlin & Marcus, P.A.

(57) ABSTRACT

The present invention relates to aprotinin variants having improved enzyme-inhibitory, immunological and pharmacokinetic properties and their preparation.

3 Claims, 1 Drawing Sheet

Fig. 1

Examples of the aprotinin variants according to the invention

Amino acid sequence

| Position | 1-58 |
|---|---|
| Aprotinin | RPDFCLEPPYTGPCKARIIRYFYNAKAGLCQTFVYGGCRAKRNNFKSAEDCMRTCGGA |
| Compound 1 | RDFCLEPPSTGPCRAAIIRYFYNATAGLCETFVYGGCRANRNNFKSAEDCMETCGGA |
| Compound 2 | RDFCLEPPSTGPCRARIIRYFYDATAGLCETFVYGGCRANRNNFKSAEDCMETCGGA |
| Compound 3 | RDFCLEPPSTGPCRASIIRYFYDATAGLCETFVYGGCRANRNNFKSAEDCMETCGGA |
| Compound 4 | RDFCLEPPSTGPCRASIIRYFYNATAGLCETFVYGGCRANRNNFKSAEDCMETCGGA |
| Compound 5 | RDFCLEPPSTGPCRASIIRYFYDATAGLCQTFVYGGCRANRNNFKSAEDCMETCGGA |

APROTININ VARIANTS HAVING IMPROVED PROPERTIES

The present invention relates to aprotinin variants having improved enzyme-inhibitory, immunological and pharmacokinetic properties and their preparation.

Aprotinin, which is also called bovine pancreatic trypsin inhibitor (BPTI), belongs to the family of serine protease inhibitors of the Kunitz type. The spectrum of the inhibitable serine proteases includes, for example, trypsin, chymotrypsin, plasmin and plasma kallikrein (W. Gebhard, H. Tschesche and H. Fritz, Proteinase Inhibitors, Barrett and Salvesen (eds.), Elsevier Science Publ. BV 375–387, 1986).

Aprotinin consists of 58 amino acids. The three-dimensional structure of the protein was elucidated with the aid of X-ray structural analysis and NMR spectroscopy (Wlodawer et al., J. Mol. Biol. 198 (3), 469–480, 1987; Wagner et al., J. Mol. Biol. 196 (1), 227–231, 1987; Berndt et al., Biochemistry 32 (17), 4564–4570, 1993).

Under the trade name Trasylol®, natural aprotinin was originally employed for the treatment of pancreatitis. Trasylol® is today used in cardiac surgery, since clinical studies have shown that treatment with aprotinin significantly decreases the need for transfusion in operations of this type and leads to the reduction of post-operative bleeding (D. Royston, J. Cardiothorac. Vasc. Anesth. 6; 76–100, 1992).

It was possible to show that the replacement of the amino acid in position 15 defining the inhibitory specificity leads to useful aprotinin variants having improved inhibitory properties (German Patent Specification 3 339 693). Depending on the amino acid introduced, in this way potent inhibitors can be produced which, for example, inhibit the elastase from pancreas or from leucocytes.

It was further possible to show that the inhibitory properties of aprotinin and of the variants produced by replacement in position 15 is also determined by further amino acid residues in the contact region between the target protease to be inhibited and the inhibitor molecule. These especially include the additional amino acid residues in positions 14, 16, 17, 18, 19, 34, 38 and 39. Aprotinin variants having improved properties due to replacement of one or more of these amino acid residues in the area of the contact region were described, inter alia, in the following patent applications by way of example: WO 89/01968, WO 89/10374, EP 0 307 592, EP 683 229.

Interestingly, it was possible to improve the pharmacokinetic properties of aprotinin and its variants by amino acid replacements which define the physicochemical properties of the substance. It was thus possible, by lowering the positive net charge of the molecule, significantly to lower the renal binding. Variants of this type were described in the Patent Application WO 92/06111.

For reasons of better industrial preparability, it is convenient in certain cases to carry out a modification to the N-terminal end of the inhibitor molecule. Such modifications can be N-terminal contractions or extensions or deletions of one or more amino acids. N-terminally modified aprotinin variants were described in EP 419 878.

Aprotinin Variants According to the Invention

The aprotinin variants described in the present patent application are distinguished by the following features:

1. Replacement of one or more amino acids in the active centre of the molecule to improve the activity properties.

2. Replacement of amino acids to decrease the positive net charge with the aim of improving the immunological and pharmacokinetic properties.

3. Modification of the N-terminal amino acid sequence for reasons of industrial preparability.

BRIEF DESCRIPTION OF THE DRAWING

The invention will now be described in greater detail with reference to the drawing, wherein FIG. 1 is a chart comparing the amino acid sequences of various aprotinin variants according to the present invention.

Aprotinin variants which each contain only one of the features mentioned were described in the patent applications cited above. The aprotinin variants according to the invention now combine in their molecular structure two or three of the abovementioned features. The amino acid sequence is shown by way of example for some variants in the figure.

The aprotinin variants according to the invention are not restricted, however, to the examples named in FIG. 1. The aprotinin variants according to the invention also include variants with the N-terminal extension Ala(−2)-Gln(−1), with the natural amino acid residue proline in position 2, with the replacement of other amino acids which carry a positive charge by neutral or negatively charged amino acid residues, or with the replacement of other neutral amino acids by negatively charged amino acid residues. The choice of the replacements of amino acid residues here follows the principle of producing a substance which at physiological pH has a reduced positive net charge, preferably in the range from +2 to −2. The changes in the amino acid sequence mentioned, including the N-terminal extension or contractions or deletions can be utilized in any desired combination with one another. The aprotinin variants according to the invention thus include all compounds which contain a combination of the abovementioned features and at physiological pH have a reduced positive net charge.

Surprisingly, it appears that the combination of two or three of the features mentioned not only leads to the obtainment, but in some cases even to the reinforcement of the expression of the individual features. Moreover, it was possible to produce significant new substance properties which are related, for example, to the immunological, the pharmacokinetic and the surface-binding properties. The new variants show a decreased reaction with polyclonal human. and rabbit antisera which have been produced using aprotinin. It was further found that the new variants have a distinctly decreased immunogenic behaviour in comparison with aprotinin, i.e. they induce a decreased immune response. It was furthermore possible to show that the variants according to the invention induce a lower release of histamine from blood cells in comparison with aprotinin. The new variants furthermore show a distinctly lower renal accumulation in comparison with aprotinin. The enzyme-kinetic inhibition constants ($K_i$ values) have been surprisingly improved compared with earlier variants of the molecule, in spite of the large number of changes in the body of the molecule.

The present invention thus relates to aprotinin variants having a net charge of +3 to −3 at pH 7 and with the amino acids Arg 15 or Arg 15-Ala 17. Preferred variants are those having a net charge of +2 to −2, particularly preferably those having a charge of +1 to −1.

These aprotinin variants are suitable for the inhibition of plasma kallikrein, tissue kallikrein and plasmin.

In addition, these aprotinin variants can have a modified N-terminal sequence.

Thus aprotinin variants with an N-terminal extension or contraction or with deleted amino acids in the N-terminus are intended.

Preferred aprotinin variants are those from the group consisting of DesPro2-Ser10-Arg15-Ala17-Asp24-Thr26-Glu31-Asn41-Glu53-aprotinin, DesPro2-Ser10-Arg15-Asp24-Thr26-Glu31-Asn41-Glu53-aprotinin, DesPro2-Ser10-Arg15-Ser17-Asp24-Thr26-Glu31-Asn41-Glu53-aprotinin, DesPro2-Ser10-Arg15-Ala17-Thr26-Glu31-Asn41-Glu53-aprotinin and DesPro2-Ser10-Arg15-Ala17-Asp24-Thr26-Asn14-Glu53-aprotinin.

These aprotinin variants can also carry the amino acid proline in position 2.

The invention also relates to medicaments comprising one or more of these aprotinin variants.

The novel proteinase inhibitors described are suitable for the treatment of disease states in which—also as a result of relatively complex surgical methods such as, for example, in cardiac surgery or in alloarthroplastic joint replacement in transplantation medicine—activation of the plasmatic enzyme systems occurs due to extensive or intensive foreign surface contact of the blood.

The inhibitors reduce the blood loss in operations which are associated with an increased risk of bleeding (e.g. heart operations, bone and joint surgery). They are suitable for therapy in the case of shock, polytrauma and cranial and brain trauma, sepsis, disseminated intravasal coagulopathy (DIC), multi-organ failure, inflammatory disorders with involvement of the kallikrein system such as rheumatic joint disorders and asthma. They prevent invasive tumour growth and metastasis by inhibition of plasmin. They are also suitable for pain and oedema therapy due to inhibition of bradykinin synthesis, and for the treatment of strokes. They are also suitable for dialysis therapy and certificial organs to prevent inflammatory disorders, coagulation and increased risk of bleeding.

Preparation of the Aprotinin Variants According to the Invention

To prepare the aprotinin variants according to the invention, it is convenient to employ genetic engineering processes. To do this, using customary molecular biology methods, the genetic engineering information for the synthesis of the aprotinin variants considered in each case is introduced into a suitable microbial expressions organism. The recombinant microorganism is fermented; by choice of suitable conditions, the heterologous hereditary information is expressed. The expressed aprotinin variant is subsequently obtained from the culture broth.

Suitable host organisms for the production of the aprotinin variants according to the invention can be bacteria, yeasts or fungi. Expression can be effected intracellularly or, using suitable secretion systems, extracellularly. The aprotinin variants can be correctly processed or fussed to peptides or proteins.

Suitable systems for the expression of aprotinin variants have been described in the Patent Applications EP 683 229, WO 89/02463, WO 90/10075 and in various other patent applications of those already mentioned above.

Methods for Carrying Out the Invention
Enzymes

The enzymes used (restriction endonucleases, alkaline phosphatases from calf intestine, T4 polynucleotide kinase and T4 DNA ligase) were obtained from Boehringer Mannheim and GIBCO/BRL and employed according to the instructions of the manufacturers.

Molecular Biology Techniques

Routine cloning tasks, such as, for example, the isolation of plasmid DNA from E. coli (so-called miniprep) and the transformation of E. coli with plasmid DNA were carried out according to Sambrook et al. (Molecular Cloning Cold Spring Harbor, 1989). The host organism employed for transformations was the E. coli strain DH5α (GIBCO/BRL). To isolate larger amounts of plasmid DNA, Qiagen tips (Qiagen) were used. The extraction of DNA fragments from agarose gels was carried out with the aid of Jetsorb according to the details of the manufacturer (Genomed).

Oligonucleotides for "site-directed mutagenesis" experiments and primers for PCR and sequencing reactions were prepared using the "380 A DNA synthesizer" from Applied Biosystems. The mutagenesis experiments were carried out according to a process of Deng and Nickoloff (Deng et al., Anal. Biochem. 200, 81–88, 1992) using a kit from Pharmacia Biotech ("Unique Site Elimination Mutagenesis"). All vector constructs and mutagenesis experiments were confirmed by Taq cycle DNA sequencing using fluorescence-labelled terminators on an "ABI 373 A sequencer" (Applied Biosystems).

Transformation of Saccharomyces cerevisiae

Yeast cells, e.g. the strain JC34. 4D (MATα, ura3-52, suc2), were cultured in 10 ml of YEPD (2% glucose; 2% peptone; 1% Difco yeast extract) and harvested at an $O.D._{600\,nm}$ of 0.16 to 0.8. The cells were washed with 5 ml of solution A (1 M sorbitol; 10 mM bicine pH 8.35; 3% ethylene glycol), resuspended in 0.2 ml of solution A and stored at −70° C.

Plasmid DNA (5 μg) and carrier DNA (50 μg from herring sperm) were added to the frozen cells. The cells were then thawed by shaking for 5 min at 37° C. After addition of 1.5 ml of solution B (40% PEG 1000, 200 mM bicine pH 8.35), the cells were incubated at 30° C. for 60 min, washed with 1.5 ml of solution C (0.15M NaCl; 10 mM bicine pH 8.35) and resuspended in 100 μl. Plating-out was carried out on a selective medium with 2% agar. Transformants were obtained after an incubation of 3 days at 30° C.

| Nutrient media for the fermentation | | |
|---|---|---|
| 1. | SD2 medium: | |
| | Bacto Yeast Nitrogen Base | 6.7 g/l |
| | Glucose* | 20 g/l |
| | $KH_2PO_4$ | 6.7 g/l |
| | | pH 6.0 |
| 2. | SC5 medium: | |
| | Glucose* | 20 g/l |
| | Difco yeast extract | 20 g/l |
| | $KH_2PO_4$ | 6.7 g/l |
| | $(NH_4)_2SO_4$ | 2.0 g/l |
| | $MgSO_4 \times 7\ H_2O$ | 1.0 g/l |
| | Trace element solution SL4 | 1.0 ml/l |
| | | pH 6.0 |
| | Trace element solution SL4: | |
| | Titriplex III | 5 g/l |
| | $FeSO_4 \times 7\ H_2O$ | 2 g/l |
| | $ZnSO_4 \times 7\ H_2O$ | 0.1 g/l |
| | $MnCl_2 \times 4\ H_2O$ | 0.03 g/l |
| | $H_3BO_3$ | 0.3 g/l |
| | $CoCl_2 \times 6\ H_2O$ | 0.2 g/l |
| | $CuCl_2 \times 2\ H_2O$ | 0.01 g/l |
| | $NiCl_2 \times 6\ H_2O$ | 0.02 g/l |
| | $Na_2MoO_4 \times 2\ H_2O$ | 0.03 g/l |
| 3. | Fermenter medium: | |
| | Glucose* | 2.0 g/l |
| | Soya peptone | 25.0 g/l |
| | $KH_2PO_4$ | 1.4 g/l |
| | $MgSO_4 \times 7\ H_2O$ | 1.0 g/l |

-continued

Nutrient media for the fermentation

| | | |
|---|---|---|
| Thiamine chloride | 5.1 | mg/l |
| Inositol | 20 | mg/l |
| Trace element solution | 3 | mg/l |
| Vitamin solution | 3 | mg/l |
| $(NH_4)_2SO_4$ | 3.8 | g/l | pH 5.5

Feed solution:

| | | |
|---|---|---|
| Glucose* | 530 | g/l |
| $(NH_4)_2SO_4$ | 5.0 | g/l |
| $KH_2PO_4$ | 2.9 | g/l |
| $MgSO_4 \times 7 H_2O$ | 3.8 | g/l |
| Thiamine chloride | 13 | mg/l |
| Inositol | 70 | mg/l |
| Trace element solution | 6.8 | ml/l |
| Vitamin solution | 6.8 | ml/l |

Trace element solution:

| | | |
|---|---|---|
| $FeCl_3 \times 6 H_2O$ | 13.5 | g/l |
| $ZnCl_2 \times 4 H_2O$ | 2.0 | g/l |
| $H_3BO_3$ | 0.5 | g/l |
| $CoCl_2 \times 6 H_2O$ | 2.0 | g/l |
| $CuSO_4 \times 5 H_2O$ | 1.9 | g/l |
| $Na_2MoO_4 \times 2 H_2O$ | 2.0 | g/l |
| $CaCl_2 \times 2 H_2O$ | 1.0 | g/l |
| HCl conc. | 100 | ml/l |

Vitamin solution:

| | | |
|---|---|---|
| Riboflavin | 0.42 | g/l |
| Ca pantothenate | 5.9 | g/l |
| Nicotinic acid | 6.1 | g/l |
| Pyridoxine hydrochloride | 1.7 | g/l |
| Biotin | 0.06 | g/l |
| Folic acid | 0.04 | g/l |

*= autoclave separately

Preparation of Working Preserves

Using a stock preserve, 200 ml of SD2 medium in a 1 l Erlenmeyer flask were inoculated to a concentration of 1%. The culture was incubated for 72 hours at 28° C. on the shaker (260 rpm). 2 ml each were then filled into preserve containers and frozen in liquid nitrogen.

Fermentation in the Shaker Flask

As a preculture, 200 ml of SD2 medium were inoculated to 1% with a working preserve in a 1 l flask and fermented for 72 hours at 28° C. on the shaker (260 rpm). Using the preculture, main cultures (200 ml of SC5 medium in 1 l flasks) were inoculated to a concentration of 1% and incubated for 72–96 hours on the shaker at 28° C.

Fermentation in 10 l Bioreactors

As a preculture, 200 ml of SD2 medium were inoculated in a 1 l flask to a concentration of 1% with a working preserve and fermented for 72 hours at 28° C. on the shaker (260 rpm). The main culture in the 10 l fermenter was carried out as a fed-batch fermentation over the course of 96 hours. The nutrient medium used was fermenter medium and the starting volume was 7 l. The fermenter was inoculated with 200 ml of preculture.

Fermentation Conditions

Temperature: 28° C.
Rotational speed of stirrer: 500 rpm
Aeration: 10 l/min
pH: 5.5
Head space pressure: 200 mbar After a fermentation time of 7 hours, feeding was started. The feed rate was controlled via the respiratory quotient (RQ) (RQ=$CO_2$ formed/oxygen consumed). If the RQ climbed to values of >1.15, the feed rate was lowered, if it fell to values of <1.05 the feed rate was increased.

At regular intervals, samples were removed from the fermenter and the cell growth was determined by measurement of the optical density at 700 nm. Additionally, the concentration of Bay 19-8757 in the supernatant was determined by activity measurement.

At the end of the fermentation, the pH was lowered to 3.0 by addition of 50% (w/v) citric acid and the fermenter was heated at 70° C. for 10 min. The cells were then separated off by centrifugation at 7,500×g and the supernatant was handed over for protein purification.

Materials for Protein Chemical Analysis

The sequence analyses were carried out using a protein sequencer model 473A from Applied Biosystems (Forster City, USA). The standard sequencing programme was used. The sequencer, the various sequencing programmes and the PTH detection system are described in detail in the operating handbook (User's manual protein sequencing system model 473 A) (1989) Applied Biosystems Forster City, Calif. 94404, USA).

The reagents for the operation of the sequencer and the HPLC column for PTH detection were obtained from Applied Biosystems.

The HPLC analyses were carried out using an AP 1090 HPLC system from Hewlett Packard (D-Waldbronn). An RP-18 HPLC column (250 mm×4.6 mm, 5$\mu$ material, 300 Angström pore diameter) from Backerbond (D-Groß Gerau) was used for the separation.

The capillary electrophoresis Model 270 A-HT was from Applied Biosystems (Forster City, Calif. 94404, USA). As a rule, the samples were injected hydrodynamically over various time intervals. The capillary column used (50 $\mu$m×72 cm) was from Applied Biosystems.

The amino acid analyses were carried out with an amino acid analyser LC 3000 from Eppendorf Biotronik (D-Maintal). A slightly modified standard separation programme from Biotronik was used. The separation programme and the function of the analyser are described in detail in the apparatus handbook.

The molecular weights were determined with a MALDI I system from Kratos/Shimadzu (D-Duisburg). The SDS electrophoreses were carried out with an electrophoresis system from Pharmacia (D-Freiburg).

The determination of the kinetic data was carried out with the microtitre plate reader from SLT (D-Crailsheim). The washing of the microtitre plates was carried out with a washing apparatus from Dynatec (D-Denkendorf).

Enzymes and substrates were from Calbiochem (D-Bad Soden). All other chemicals and reagents were from Merck (D-Darmstadt) or Sigma (D-Deisenhofen). 96-well plates were obtained from Greiner.

The polyclonal rabbit anti-aprotinin antibodies were raised in rabbits by immunization with aprotinin. The human polyclonal anti-aprotinin antibodies come from patients who were treated with aprotinin.

Protein Chemical Analysis

N-terminal Sequence Analysis

1–3 nmol of protease inhibitor dissolved in water were loaded on a sequencer sheet which was preincubated with Polybrene. The protein was sequenced using the fast normal sequencer cycle. The PTH amino acids were identified by means of online HPLC with the aid of a 50 pmol PTH, standard.

Amino Acid Analysis

200 µg of protein were dissolved in 200 µl of 6N HCl and hydrolysed for 1 h at 166° C. About 1 nmol of the sample was added to the amino acid analyser. The amount of amino acid was determined by means of a 5 nmol standard.

SDS Gel Electrophoresis

The SDS gel electrophoresis was carried out according to the conditions of Laemmli. 10 µg of the protease inhibitor were analysed using a 10–20% strength SDS gel and visualized by means of silver staining (Merril et al.).

U. K. Laemmli, Nature 227, 680–685 (1970).

C. R. Merril, M. L. Dunau, D. Goldmann, Anal. Biochem. 100: 201–207 (1981).

Capillary Electrophoresis 8 ng of the protease inhibitor were investigated by means of capillary electrophoresis on a glass column (length 72 cm, internal diameter 50 µm). Conditions: current density 90 µA, column temperature 25° C., 100 nM phosphate buffer pH 3.0, detection 210 nm, loading under pressure 3 sec.

Reverse-phase Chromatography 5 nmol of the protease inhibitor were chromatographed on a Bakerbond RP-18 HPLC column (5µ material, 4.6 nm×250 mm, 300 Angström pore size). The eluent used was an acetonitrile/TFA gradient. Conditions: flow rate 0.7 ml/min, column temperature 40° C., detection 40° C., solvent A 0.1% TFA, Solvent B 0.1% TFA/60% acetonitrile; gradient: 0 min 0% B, 10 min 0% B, 70 min 100% B, 80 min 0% B.

Molecular Weight Determination

1 µg of the protease inhibitor was analysed using the MALDI technique. The matrix used was sinapic acid. The standard proteins for mass calibration were bovine insulin, cytochrome C and melittin.

Protein Content

The protein content is determined according to the BCA method. In this method, $Cu^{2+}$ ions are reacted by means of the proteins present to give $Cu^{1+}$ ions which form a complex with bicinchoninic acid, which absorbs at 560 nm.

The lyophilized protein is brought to equilibrium moisture content and dissolved in 0.9% NaCl solution at a concentration of 1 mg/ml. A dilution series is prepared. 1000 µl of BCA test reagent (Pierce) are added to 50 µl of sample solution, and the test tube is firmly closed with a stopper and incubated at 60° C. for exactly 30 minutes. After cooling the samples in an ice bath for 5 minutes, measurement is carried out at a temperature of 25° C. and a wavelength of 560 nm.

Activity: (Trypsin Inhibition Test, Titrimetric)

The activity is determined according to a modified F.I.P. trypsin inhibition test. Bay y 19-8757 inhibits the trypsin-catalysed hydrolysis of Nα-benzoyl-L-arginine ethyl ester (BAEE). The carboxyl groups liberated in the reaction are determined by the alkali titration. The trypsin residual activity is a measure of the inhibitory activity of the active compound.

The lyophilized protein is brought to equilibrium moisture content, dissolved in 0.9% NaCl solution at a concentration of 1 mg/ml and a dilution series is prepared. 2 ml of buffer (15 mM borate buffer, pH 8.0 containing 200 mM $CaCl_2$) and 0.8 ml of trypsin solution (2 mg/ml) are added to 1 ml of sample solution and the mixture is incubated at 25° C. for 5 minutes. 0.2 ml of BAEE solution (6.8 mg/ml) is then added and the KOH consumption is measured over the course of 5 minutes.

Determination of the Cross-reaction of the Protease Inhibitors with Polyclonal Rabbit or Human Anti-aprotinin Antibodies 0.5–10 ng of protease inhibitor or aprotinin dissolved in coupling buffer were bound overnight at 4° C. to a microtitre plate. The wells were washed 4 times with 200 µl of wash buffer each time and 100 µl of the blocking solution were then added. The plate was covered and incubated at 37° C. for one hour. After washing as described above, the polyclonal rabbit anti-aprotinin antibodies (0.2 µg/ml in 1% BSA in PBS buffer) or the polyclonal human antibodies (20 µg/ml in 1% HSA in PBS buffer) were added. The plate was covered and incubated at 37° C. for one hour and then washed as described above. 100 µl of biotinylated anti-rabbit or anti-human antibody (25 µl+10 ml of 1% BSA or 1% HSA in PBS buffer) were then added and the mixture was incubated at 37° C. for one hour. The plate was washed as described above and 100 µl of streptavidin-peroxidase complex (50 µl+10 ml of 1% BSA or 1% HSA in PBS buffer) were then added to each well. The plate was covered and incubated at 37° C. for one hour and then washed as described above.

The substrate reaction was carried out with TMB substrate+peroxidase solution (1+1; 100 µl per well). The reaction was stopped after 10 min using 100 µl/well of 2 M phosphoric acid and the absorption was measured at 450 nm (reference 570 nm).

Solutions

1. Incubation buffer: 15 nM $Na_2CO_3$, 35 mM $NaHCO_3$, pH 9.6
2. Sample buffers: The samples were dissolved in the incubation buffer at a suitable concentration.
3. Wash solution: 0.1% (v/v) Tween 20 in PBS
4. Blocking buffer: 3% (w/v) BSA or HSA in PBS.

EXAMPLES

Example 1

Preparation of a Yeast Expression Vector for the Secretion of Recombinant DesPro2-Ser10-Arg15-Ala17-Asp24-Thr26-Glu31-Asn41-Glu53-aprotinin The starting material used for the preparation of the DesPro2-Ser10-Arg15-Ala17-Asp24-Thr26-Glu31-Asn41-Glu53-aprotinin gene was a DesPro2-Arg15-Ala17 gene, which was cloned into the vector pUC18 by means of the restriction enzymes HindIII and BamHI. The resulting vector (pEM6.6.L) was subjected to a double strand mutagenesis reaction according to the U.S.E. process (Pharmacia Biotech) with the mutagenesis primer A and the ScaI/MluI U.S.E. selection primer. The mutagenesis primer A had the following sequence:

Primer A

5' G G C T G C A G A G C T A A C C G T A A C A A C T-TCAAATCCGCGGAAGACTGCATGG AAACTTGCG-GTGGTGCTTAG 3 (SEQ ID NO: 1). This primer generates the mutations Asn41 and Glu53 in the DesPro2-Arg15-Ala17 aprotinin gene. The analysis of the clones was carried out by means of a restriction digestion using the enzymes ScaI and SphI. The desired sequence was additionally confirmed by DNA sequencing of the clone pEM31.8.L. The further replacements in the 5' area of the gene (Ser10-Asp24-Thr26-Glu31) were produced with the aid of the PCR technique using the primer B and the 'reverse 24-mer M13' primer starting from pEM31.8.L plasmid DNA. The primer B had the following sequence:

Primer B

5'TGC<u>CTCGAG</u>CCGCCGTCTACTGGGCCCTGCA GAGCTATCATCCGTTACT TACGATGCAACTGCAG-GCCTGTGTGAAACCTTCGTATACGGC 3' (SEQ ID No: 2). The Xho1 recognition sequence is underlined.

The PCR mixture contained 20 ng of pEM31.8.L plasmid DNA, 20 pmol of 'reverse 24-mer M13' primer, 60 pmol of primer B, 200 µM of dNTPs, 1×PCR reaction buffer II (Perkin Elmer), 4 mM MgCl$_2$ and 2.5 U of Taq DNA polymerase (Perkin Elmer) in a total volume of 100 µl. The 'cycle' conditions were: 3 min at 94° C., 30 cycles of, in each case, 1 min at 94° C., 1 min, at 55° C. and 1 min at 72° C. and a subsequent 5 min incubation at 72° C. The PCR mixture was diluted 1:5 and ligated with the vector pCRII (Invitrogen). Using the ligation mixture, E. coli DH5α cells were transformed. Positive clones were identified after a restriction digestion with the enzymes Xho1 and BamHI and several clones were sequenced. The clone pES9.10.L contained the desired sequence and was employed for the further studies.

An E. coli/yeast shuttle vector (e.g. pA202) was used for the construction of a yeast secretion vector in which the DesPro2-Ser10-Arg15-Ala17-Asp24-Thr26-Glu31-Asn41-Glu53-aprotinin sequence is linked to the yeast alpha-factor pre-pro sequence.

The vector pA202 carries an ampicillin resistance gene (bla) and a URA3 gene as selectable marker genes for E. coli and yeast. Further essential elements of the vector are the Col E1 and the 2µ origin of replication (ori). The REP3 locus is also situated in this region. A 1200 bp EcoRI HindIII fragment carries the MFα1 promoter and the N-terminal pre-pro sequence of the yeast alpha-factor precursor protein (Kurjan and Herskowitz, Cell, 30 933 943, 1982). By introduction of a modified DesPro2-Arg15-aprotinin cDNA as a HindIII-BamHI fragment, the recognition sites for the KexII protease ('Lys-Arg') within the alpha-factor pre-pro sequence was again prepared (EP 0 419 878).

At the 3' end of the DesPro2-Arg15-aprotinin sequence, the vector carries a BamHI-saII fragment of the yeast URA3 gene, which functions in this position as a termination signal for transcription (Yarger et al., Mol. Cell. Biol. 6, 1095–1101, 1986).

A 180 bp DNA fragment was excised from the vector pES9.10.L with Xho1 and BamHI, purified by means of agarose gel electrophoresis and cloned into the vector pA202 which was also cleaved with Xho1 and BamHI and dephosphorylated. By means of this cloning, the DesPro2-Arg15-aprotinin in the vector pA202 is replaced by the DesPro2-Ser10-Arg15-Ala17-Asp24-Thr26-Glu31 -Asn41-Glu53-aprotinin. Yeast cells (JC34.4D) were cloned using the vector pES13.10.L resulting from this cloning.

Other E.coli/yeast shuttle vectors with different promoters, such as, for example, the constitutive GAPDH or the inducible GAL 10 promoter, can be prepared in a similar manner and also lead to the secretion of DesPro2-Ser10-Arg15-Ala17-Asp24-Thr26-Glu31-Asn41-Glu53-aprotinin.

In addition, it is of course also possible to employ shuttle vectors with other yeast replication origins, such as, for example, the segment (ars) which autonomically replicates chromosomally.

Besides the URA3 gene, suitable selectable marker genes are those genes which help an auxotrophic yeast mutant to prototrophy, such as, for example, the LEU2, HIS3 or TRP1 genes. Additionally, genes can of course also be employed whose products impart resistance to various antibiotics, such as, for example, the aminoglycoside G418.

Other yeasts, such as, for example, the methylotrophic yeasts Pichia pastoris or Hansenula polymorpha, are also able, after transformation with suitable vectors, to produce DesPro2-Ser10-Arg15-Ala17-Asp24-Thr26-Glu31-Asn41-Glu53-aprotinin.

Example 2

Preparation of a Yeast Expression Vector for the Secretion of Recombinant Ser10-Arg15-Ala17Asp24-Thr26-Glu31-Asn41-Glu53-aprotinin with the Natural N-terminal Sequence 'Arg-Pro-Asp'

For the preparation of a yeast expression vector which allows the secretion of Ser10-Arg15-Ala17-Asp24-Thr26-Glu31-Asn41-Glu53-aprotinin with the natural N-terminal sequence 'Arg-Pro-Asp', the MFα1 promoter with the α-factor pre-sequence and the 5' end of the aprotinin gene (up, to the recognition sequence of the restriction enzyme Xho1) was first amplified by means of PCR and cloned. The primers used had the following sequence:

Primer C:
5'GGGATATCTATTGATAAGATTTAAAGGTATTT GACAAG 3' (SEQ ID NO; 3). The EcoRV recognition sequence is underlined.

Primer D:
5'GGGCTCGAGGCAGAAATCTGGTCTAGCCAAA GCAGAAGAAGCAGCGAAC AAGACAGCAGT-GAAAATAG ATG GAATCTCATTCTTT-TAATCGTTTATATT 3' (SEQ ID NO. The Xho1 recognition sequence is underlined.

The PCR mixture contained 200 ng of pA202 plasmid DNA, 0.2 µM primer C, 0.2 µM primer D, 200 µM dNTPs, 1×PCR reaction buffer 11 (Stratagene, Opti-Prime™) and 2.5 U of Taq DNA polymerase (Perkin Elmer) in a total volume of 50 µl. The 'cycle' conditions were: 1 min at 94° C., 30 cycles with, in each case, 1 min at 94° C., 1 min at 50° C. and 2 min at 72° C. and a subsequent 5 min incubation at 72° C. The PCR mixture was diluted 1:5 and ligated with the vector pCRII (Invitrogen). Using the ligation mixture, E. coli DH5α cells were transformed. Positive clones were identified after a restriction digestion with the enzyme EcoRI and several clones were sequenced. The clone pIU20.11.L was employed for the further studies.

The E. coli /yeast shuttle vector pYES2 (Invitrogen) was used for the construction of a yeast secretion vector in which the Ser10-Arg15-Ala17-Asp24-Thr26-Glu31-Asn41-Glu53-aprotinin sequence is linked directly to the yeast alpha-factor pre-sequence. The vector pYES2 was first cleaved with the restriction enzymes SspI and BamHI, dephosphorylated and gel-purified. The GAL1 promoter present on the vector pYES2 and the f1 ori are removed in this way. An about 1030 bp DNA fragment was excised with EcoRV and Xho1 from the vector pIU20.11.L, purified by means of agarose gel electrophoresis and cloned together with an about 180 bp Xho1 and BamHI fragment from the vector pES9.10.L into the vector pYES2 cleaved with SspI and BamHI. Using the ligation mixture, E. coli DH5α cells were transformed. Positive clones were identified and sequenced after a restriction digestion with the enzyme Xho1. Yeast cells (JC34.4D) were transformed using the vector pIU28.11.L resulting from this cloning. The expression vector pIU28.11.L no longer contains an α-factor pro-sequence, so that the processing of the Ser10-Arg15-Ala17-Asp24-Thr26-Glu31-Asn41-Glu53-aprotinin takes place exclusively by means of the signal peptidase and is independent of the cleavage by the KexII protease.

Example 3

Fermentation of Saccharomyces cerevisiae

A Saccharomyces cerevisiae expression strain was fermented as described above.

Example 4

Purification of Aprotinin Derivatives without Net Charge at Neutral pH

1. Survey of Suitable Purification Processes

After the fermentation, the cells are separated off by centrifugation and the supernatant which remains is filtered in, order to remove remaining cells.

The cell-free supernatant is adjusted to pH 3 by addition of concentrated citric acid. The solution must be suitably diluted with purified water in order to establish a conductivity of less than 8 mS/cm. Subsequently, the solution is applied to a cation exchanger column, which has previously been equilibrated with an acid buffer. Unbound material is removed by copious washing with starting buffer. The product is eluted with the aid of a salt gradient. The fractions obtained are investigated further for their product content with the aid of reverse-phase high-pressure liquid chromatography (RP-HPLC) and a biological activity test which determines the protease inhibition. Fractions which contain the product are combined and applied directly to a preparative RP-HPLC column. The column was previously equilibrated with an acidic buffer. Unbound protein is removed by washing the column with starting buffer. The product is eluted with the aid of an organic solvent gradient. The fractions are again investigated further for their product content as already described above and those fractions which contain product are combined. Depending on the purity of the product achieved, it may possibly be necessary to purify the combined fractions on a second RP-HPLC column. The conditions are essentially the same as those already described. The product solution obtained is diluted with water for injection purposes and dispensed in suitable portions and freeze-dried.

Other methods for the purification of aprotinin derivatives without net charge at neutral pH which can be combined with the processes described above are affinity chromatography on Sepharose-immobilized trypsin and gel permeation chromatography.

2. Purification of DesPro2-Ser10-Arg15-Ala17-Asp24-Thr26-Glu31-Asn41-Glu53-aprotinin Material from 10 l fermentations was purified according to the following process. After the fermentation was complete, the fermenter contents were adjusted to pH 3 using concentrated citric acid and heated at 70° C. for 10 minutes. The cells were then removed by centrifugation, (15 minutes, 7500×g, Heraeus centrifuge) and the supernatant obtained was filtered (8 μm to 0.2 μm, Millipore, Germany). From this stage, the supernatant can be stored until further use by freezing at −18° C. The solution was then diluted to a conductivity of less than 8 mS/cm by addition of purified water and applied to an SP-sepharose FF column, (Pharmacia, Sweden). The column had previously been equilibrated with 50 nM citrate-NaOH buffer, pH 3. Unbound protein was removed by intensive washing with the same buffer. The product was then eluted with the aid of a salt gradient (1 M NaCl). The fractions obtained were investigated for their product content with the aid of reverse-phase high-pressure liquid chromatography (RP-HPLC, C4) and by testing of the protease inhibition activity. Those fractions which contain the desired product were combined.

The product solution was then applied directly to the first RP-HPLC column (Source 15 RPC, Pharmacia, Sweden), which had previously been equilibrated with 0.1% trifluoroacetic acid/water. Unbound protein was removed by intensive washing with the same buffer. The product was eluted with the aid of a linear acetonitrile gradient (0–70%). The fractions obtained were again investigated for the product content using the methods described above and those which contained product were combined.

For the final purification, the product-containing solution was diluted with water for injection purposes and applied to the second RP-HPLC column (Vydac C8, Vydac, USA), which had previously been equilibrated with 0.1% trifluoroacetic acid/water. Unbound protein was removed by intensive washing with the same buffer. The product was eluted with the aid of a linear acetonitrile gradient (0–70%). The fractions obtained were again investigated for the product content using the methods described above and those which contained product were combined.

The product solution obtained was diluted with water for injection purposes, dispensed in suitable portions (20, 10, 1 and 0.2 mg), lyophilized and analysed.

Example 5

Determination of the $K_i$ of Human Plasma Kallikrein Using DesPro-Ser10-Arg15-Ala17-Asp24-Thr26-Glu31-Asn41-Glu53-aprotinin Example:

1 unit of human plasma kallikrein was diluted to 16 ml with buffer (0.05 M tris/0.1 M NaCl, 0.05% Tween 20; pH 8.2). 200 μl of this enzyme solution were mixed with decreasing, volumes of test buffer (250, 240, 230, 220, 200, 180, 170, 150, 100 and 50 μl) and then increasing amounts of inhibitor in the assay buffer were added (10, 20, 30, 50, 70, 80, 100, 150, 200 and 250 μl; concentration 0.7 μg/μl).

The enzyme/inhibitor solution was preincubated at room temperature for 4 hours. 180 μl of each solution was then added to the well of a microtitre plate and mixed with 20 μl of substrate solution. The change in the absorption was measured at 405 nm for 10 min. The rate of the enzyme reactions was determined and the $K_i$ value was calculated from this according to the method of Bieth (Biochemical Medicine 32: 387–97 (1984)).

Substrate stock solution: 0.1 M in DMSO

Substrate solution: $1 \times 10^{-3}$ M S-2302 in assay buffer

Assay buffer: 0.05 M tris-(hydroxymethyl)-aminomethane, 0.1 M NaCl, 0.05% Tween 20; pH 8.2; 1 ml of benzyl alcohol/l.

The kinetic constants of the complexation with the enzymes plasmin factor XIa, bovine trypsin and chymotrypsin were determined by the same procedure. The substrates were Chromozym PL for plasmin, HD-Pro-Phe-Arg-pNA for factor XI, S-2444 for trypsin and Suc-Phe-Leu-Phe-pNA for chymotrypsin.

Example 6

Results of the Protein Chemical Characterization of DesPro2-Ser10-Arg15-Ala17-Asp24-Thr26-Glu31-Asn41-Glu53-aprotinin The protease inhibitor DesPro2-Ser10-Arg15-Ala17-Asp24-Thr26-Glu31-Asn41-Glu53-aprotinin was prepared by secretion by means of a yeast organism modified by genetic engineering. It was purified to homogeneity from the yeast supernatant by various chromatographic processes. The identity of the inhibitor with the cloned sequence is shown by the following protein analytical investigations.

N-terminal Sequence Analysis

The protease inhibitor was completely sequenced over 57 steps. The following list shows the protein sequence determined, which is identical to the cloned sequence.

1
Arg-Asp-Phe-Cys-Leu-Glu-Pro-Pro-Ser-Thr-Gly-Pro-Cys-Arg-Ala-Ala-Ile-Ile-Arg-Tyr-
21
Phe-Tyr-Asp-Ala-Thr-Ala-Gly-Leu-Cys-Glu-Thr-Phe-Val-Tyr-Gly-Gly-Cys-Arg-Ala-
40
Asn-Arg-Asn-Asn-Phe-Lys-Ser-Ala-Glu-Asp-Cys-Met-Glu-Thr-Cys-Gly-Gly-Ala (SEQ ID NO:5)
Sequence analysis of DesPro2-Ser10-Arg15-Ala17-Asp24-Thr26-Glu31-Asn41-Glu53-aprotinin over 57 steps.

Amino Acid Analysis

Amino acid analysis is an important quantitative parameter for the characterization of a protein. Besides the protein content, in the case of known primary structure, the number of individual amino acids is determined. The amino acid analysis of DesPro2-Ser10-Arg15-Ala17-Asp24-Thr26-Glu31-Asn41-Glu53-aprotinin is in good agreement with the theoretical values from the primary structure (Tab. 1).

TABLE 1

Amino acid analysis of
DesPro2—Ser10—Arg15—Ala17—Asp24—Thr26—Glu31—Asn41—Glu53-aprotinin. The number of residues are based on Ala = 7.

| Amino acid | Number of residues | Theoretical numbers |
| --- | --- | --- |
| $CysSO_3H$ | 5.28 | 6 |
| Asp | 6.27 | 6 |
| Thr | 3.49 | 4 |
| Ser | 1.58 | 2 |
| Glu | 4.25 | 4 |
| Gly | 6.16 | 6 |
| Ala | 7.00 | 7 |
| Val | 0.98 | 1 |
| Met | 1.10 | 1 |
| Ile | 1.66 | 2 |
| Leu | 1.89 | 2 |
| Tyr | 2.49 | 3 |
| Phe | 4.11 | 4 |
| Lys | 1.05 | 1 |
| Arg | 4.73 | 5 |
| Pro | 3.23 | 3 |

*) Cysteine and methionine were determined by performic acid oxidation (Met as methionine sulphone).

Reverse-Phase Chromatography

In the HPLC chromatography of proteins on chemically bonded reverse phases, binding to the phase used occurs via a hydrophobic interaction of the proteins. The proteins are displaced by organic solvents (mobile phase) according to the strength of their binding to the stationary phase. For this reason, this method is a good criterion for the assessment of the purity of a protein. DesPro2-Ser10-Arg15-Ala17-Asp24-Thr26-Glu31-Asn41-Glu53-aprotinin elutes as a single peak from the RP-18 phase. It was shown that the isolated protease inhibitor is very clean.

CE Chromatography

Capillary electrophoresis allows the separation of peptides and proteins on the basis of their charge in an electrical field. The quality of the separation in this case depends on the buffer, the pH, the temperature and the additives used. The capillaries employed are so-called "fused silica" columns having an internal diameter of 50–100 µm. DesPro2-Ser10-Arg15-Ala17-Asp24-Thr26-Glu31-Asn41-Glu53-aprotinin was separated on a "fused silica" column in an electrical field. The electropherogram shows a narrow peak.

Molecular Weight Determination

The molecular weight of DesPro2-Ser10-Arg15-Ala17-Asp24-Thr26-Glu31-Asn41-Glu53-aprotinin was determined to be 6223 daltons using the MALDI technique. In this case, the molecular weight determined is in good agreement with the theoretical value of 6215 daltons within the bounds of the accuracy of the measuring method. Sinapic acid was employed as a matrix.

SDS Gel Electrophoresis

DesPro2-Ser10-Arg15-Ala17-Asp24-Thr26-Glu31-Asn41-Glu53-aprotinin was analysed under reducing and non-reducing conditions by means of SDS electrophoresis. It shows a band in the range of about 6.5 kD.

Example 7

Determination of the $k_i$ Values for the Complexation of Enzymes with DesPro2-Ser10-Arg15-Ala17-Asp24-Thr26-Glu31-Asn41-Glu53-aprotinin The inhibitory constants of DesPro2-Ser10-Arg15-Ala17-Asp24-Thr26Glu31-Asn41-Glu53-aprotinin were determined for various enzymes. Table 2 shows the $k_i$ values.

TABLE 2

Inhibitory constants of the complexation of
DesPro2—Ser10—Arg15—Ala17—Asp24—Thr26—Glu31—Asn41—Glu53-
aprotinin with the enzymes and plasma kallikrein, factor XIa, bovine chymotrypsin
and bovine trypsin.

| Enzyme | $k_i$ [M] |
| --- | --- |
| Plasma kallikrein | $2 \times 10^{-11}$ |
| Plasmin | $5 \times 10^{-10}$ |
| Factor XIa | $5 \times 10^{-10}$ |
| Trypsin | $2 \times 10^{-11}$ |
| Chymotrypsin | $9 \times 10^{-9}$ |

Example 8

Interaction of the Protease Inhibitors with Polyclonal Rabbit or Human Anti-aprotinin Antibodies The protease inhibitors prepared by recombinant methods were investigated further for their cross-reactivity using polyclonal rabbits or human anti-aprotinin antibodies. It was found that the various protease inhibitor variants only show a very weak interaction with the aprotinin antisera.

---

What is claimed is:

1. The compound DesPro2-Ser10-Arg15-Ala17-Asp24-Thr26-Glu31-Asn41-Glu53-aprotinin, which has the amino acid sequence shown in SEQ ID No.: 5.

2. A pharmaceutical composition comprising the compound according to claim 1 and a carrier.

3. A method of treating a disease state characterized by the activation of plasmatic enzyme systems in a patient suffering therefrom, said method comprising administering to said patient an amount of the compound according to claim 1 which is effective to inhibit said enzyme.

* * * * *

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 69 Base pairs
      (B) TYPE: Nucleic Acid
      (C) STRANDEDNESS: Single
      (D) TOPOLOGY: linear (ii) MOLECULE TYPE: DNA (Genomic)

(iii) HYPOTHETICAL: NO (iv) ANTI-SENSE: NO (vi) ORIGINAL SOURCE:
      (A) ORGANISM: Primer A (xi) SEQUENCE DESCRIPTION: SEQ ID NO: 1:

```
GGCTGCAGAG CTAACCGTAA CAACTTCAAA TCCGCGGAAG           40

ACTGCATGGA AACTTGCGGT GGTGCTTAG                      69
```

(2) INFORMATION FOR SEQ ID NO: 2:

(i) SEQUENCE CHARACTERISTICS:
      (A) LENGTH: 96 Base pairs
      (B) TYPE: Nucleotide
      (C) STRANDEDNESS: Single
      (D) TOPOLOGY: Linear (ii) MOLECULE TYPE: Genomic DNA (iii) HYPOTHETICAL: NO (iv) ANTI-SENSE: NO (v) FRAGMENT TYPE: linear (vi) ORIGINAL SOURCE:
            (A) ORGANISM: Primer B (xi) SEQUENCE DESCRIPTION: SEQ ID NO: 2:

TGCCTCGAGC CGCCGTCTAC TGGGCCCTGC AGAGCTGCTA                                40

TCATCCGTTA CTTCTACGAT GCAACTGCAG GCCTGTGTGA                                80

AACCTTCGTA TACGGC                                                         96

(2) INFORMATION FOR SEQ ID NO: 3:

(i) SEQUENCE CHARACTERISTICS:
            (A) LENGTH: 38 Base pairs
            (B) TYPE: Nucleotide
            (C) STRANDEDNESS: Single
            (D) TOPOLOGY: linear (ii) MOLECULE TYPE: Genomic DNA (v) FRAGMENT TYPE: linear (vi) ORIGINAL SOURCE:
            (A) ORGANISM: Primer C (xi) SEQUENCE DESCRIPTION: SEQ ID NO: 3:

GGGATATCTA TTGATAAGAT TTAAAGGTAT TTGACAAG                                  38

(2) INFORMATION FOR SEQ ID NO: 4:

(i) SEQUENCE CHARACTERISTICS:
            (A) LENGTH: 100 Base pairs
            (B) TYPE: Nucleotide
            (C) STRANDEDNESS: Single
            (D) TOPOLOGY: linear (ii) MOLECULE TYPE: Genomic DNA (iii) HYPOTHETICAL: NO (iv) ANTI-SENSE: NO (v) FRAGMENT TYPE: linear (vi) ORIGINAL SOURCE:
            (A) ORGANISM: Primer D (xi) SEQUENCE DESCRIPTION: SEQ ID NO: 4:

GGGCTCGAGG CAGAAATCTG GTCTAGCCAA AGCAGAAGAA                                40

GCAGCGAACA AGACAGCAGT GAAAATAGAT GGGAATCTCA                                80

TTCTTTTAAT CGTTTATATT                                                     100

(2) INFORMATION FOR SEQ ID NO: 5:

(i) SEQUENCE CHARACTERISTICS:
            (A) LENGTH: 57 Amino acids
            (B) TYPE: Amino acid
            (C) STRANDEDNESS: Single
            (D) TOPOLOGY: linear (ii) MOLECULE TYPE: Peptide (v) FRAGMENT TYPE: linear (vi) ORIGINAL SOURCE:
            (A) ORGANISM: Aprotinin variant (xi) SEQUENCE DESCRIPTION: SEQ ID NO: 5:

-continued

```
Arg Asp Phe Cys Leu Glu Pro Pro Ser Thr Gly Pro Cys Arg Ala Ala
1               5                   10                  15

Ile Ile Arg Tyr Phe Tyr Asp Ala Thr Ala Gly Leu Cys Glu Thr Phe
            20                  25                  30

Val Tyr Gly Gly Cys Arg Ala Asn Arg Asn Asn Phe Lys Ser Ala Glu
        35                  40                  45

Asp Cys Met Glu Thr Cys Gly Gly Ala
    50                  55
```